US00PP27513P2

(12) United States Plant Patent
Williams

(10) Patent No.: US PP27,513 P2
(45) Date of Patent: Dec. 27, 2016

(54) ***CALADIUM* PLANT NAMED 'POISON DART FROG'**

(50) Latin Name: ***Caladium* hybrid**
Varietal Denomination: Poison Dart Frog

(71) Applicant: Brian Paul Williams, Louisville, KY (US)

(72) Inventor: Brian Paul Williams, Louisville, KY (US)

(73) Assignee: BRIAN'S BOTANICALS, Louisville, KY (US)

( * ) Notice: Subject to any disclaimer, the term of this patent is extended or adjusted under 35 U.S.C. 154(b) by 51 days.

(21) Appl. No.: 14/544,734

(22) Filed: Feb. 10, 2015

(51) Int. Cl.
*A01H 5/12* (2006.01)

(52) U.S. Cl.
USPC ..... Plt./373

(58) Field of Classification Search
USPC ..... Plt./263.1, 373
See application file for complete search history.

*Primary Examiner* — Susan McCormick Ewoldt
*Assistant Examiner* — Karen Redden
(74) *Attorney, Agent, or Firm* — Penny J. Aguirre

(57) ABSTRACT

A new cultivar of *Caladium* plant named 'Poison Dart Frog', that is characterized by its compact, medium-sized plant habit growing 30 to 60 cm in height, its sagittate-shaped leaves that are dark green overlaid with large reddish-pink blotches and sporadically with small white spots in color, it petioles that are dark green in color, its healthy root system, its ability to grow well in full sun where its leaves develop a reflective sheen, and its production of very large tubers as it ages.

2 Drawing Sheets

Botanical classification: *Caladium* hybrid.
Cultivar designation: 'Poison Dart Frog'.

BACKGROUND OF THE INVENTION

The present invention, *Caladium* 'Poison Dart Frog', relates to a new and distinct interspecific hybrid of *Caladium*, hereinafter referred to by its cultivar name, 'Poison Dart Frog'. 'Poison Dart Frog' is a new tropical plant used as a landscape and container plant in tropical and subtropical areas.

The new cultivar was derived from a controlled breeding program conducted by the Inventor at his nursery in Louisville, Ky. The overall purpose of the breeding program is to make selections of *Caladium* plants with unique coloration and good plant vigor. 'Poison Dart Frog' arose from a cross made in August of 2012 between unnamed proprietary *Caladium* hybrid plants (not patented) from the Inventor's breeding program as both the female and male parents. 'Poison Dart Frog' was selected as a single unique plant in July of 2013 from amongst the seedlings derived from the above cross.

Asexual propagation of the new cultivar was first accomplished by in vitro propagation using meristematic tissue under the direction of the Inventor in Eustis, Fla. in February of 2014. Asexual propagation by in vitro propagation has shown that the characteristics of the new cultivar are stable and reproduced true to type in successive generations.

SUMMARY OF THE INVENTION

The following traits have been repeatedly observed and represent the characteristics of the new cultivar. These attributes in combination distinguish 'Poison Dart Frog' as a new and unique cultivar of *Caladium*.

1. 'Poison Dart Frog' exhibits a compact, medium-sized plant habit reaching 30 to 60 cm in both height and width.
2. 'Poison Dart Frog' exhibits sagittate-shaped leaves that are dark green overlaid with large reddish-pink blotches and sporadically with small white spots in color.
3. 'Poison Dart Frog' exhibits petioles that are dark green in color.
4. 'Poison Dart Frog' exhibits a healthy root system.
5. 'Poison Dart Frog' grows well in full sun where its leaves develop a reflective sheen.
6. 'Poison Dart Frog' exhibits the production of very large tubers as it ages.

The female parent of 'Poison Dart Frog', differs from 'Poison Dart Frog' in having leaves that are overlaid with less red blotches, in having leaves that are more regularly covered with small white spots, in producing medium-sized tubers, and in having leaves with a dull surface. The male parent of 'Poison Dart Frog' differs from 'Poison Dart Frog' in being much shorter in height, in having leaves that are overlaid with fewer reddish-pink blotches, and no white spots. 'Poison Dart Frog' can be most closely compared to the *Caladium* cultivars 'Miss Muffet' (not patented) and 'Gingerland' (not patented). 'Miss Muffet' differs from 'Poison Dart Frog' in being shorter in height, in having petioles that are dark brown in color, in having leaves that are off white with small red spots in color, in being susceptible to leaf burn in full sun, in having less leaves per tuber, and in having leaves with a dull surface. 'Gingerland' differs from 'Poison Dart Frog' in having leaves that are off white in color with red to pink spots and a green rim on the margins and in having a shorter plant height.

BRIEF DESCRIPTION OF THE DRAWINGS

The accompanying colored photographs illustrate the overall appearance and distinct characteristics of the new

*Caladium*, 'Poison Dart Frog'. The photographs were taken of two year-old plants as grown in the ground in full sun under 2 mm poly in Louisville, Ky.

Figure 1:
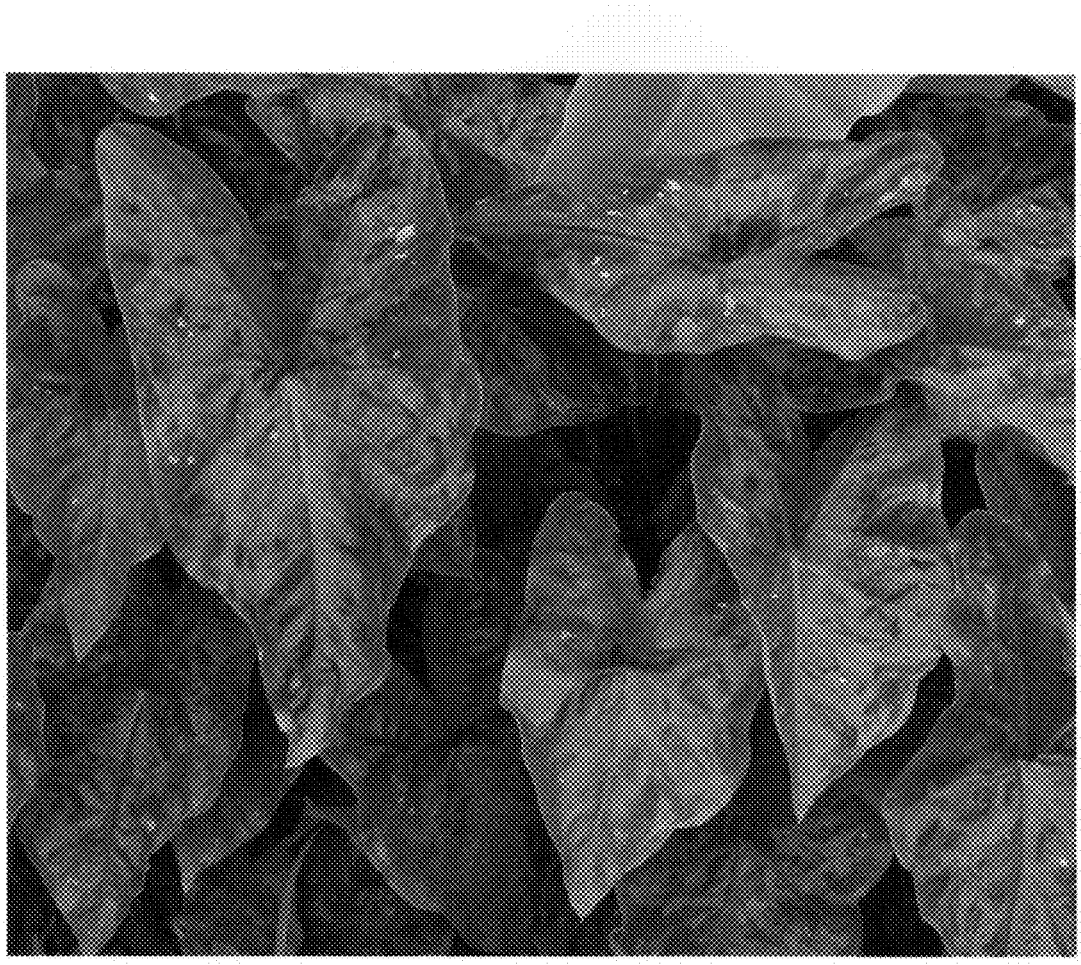

The photograph in FIG. 1 provides an overall view of the mature foliage of 'Poison Dart Frog'.

Figure 2:
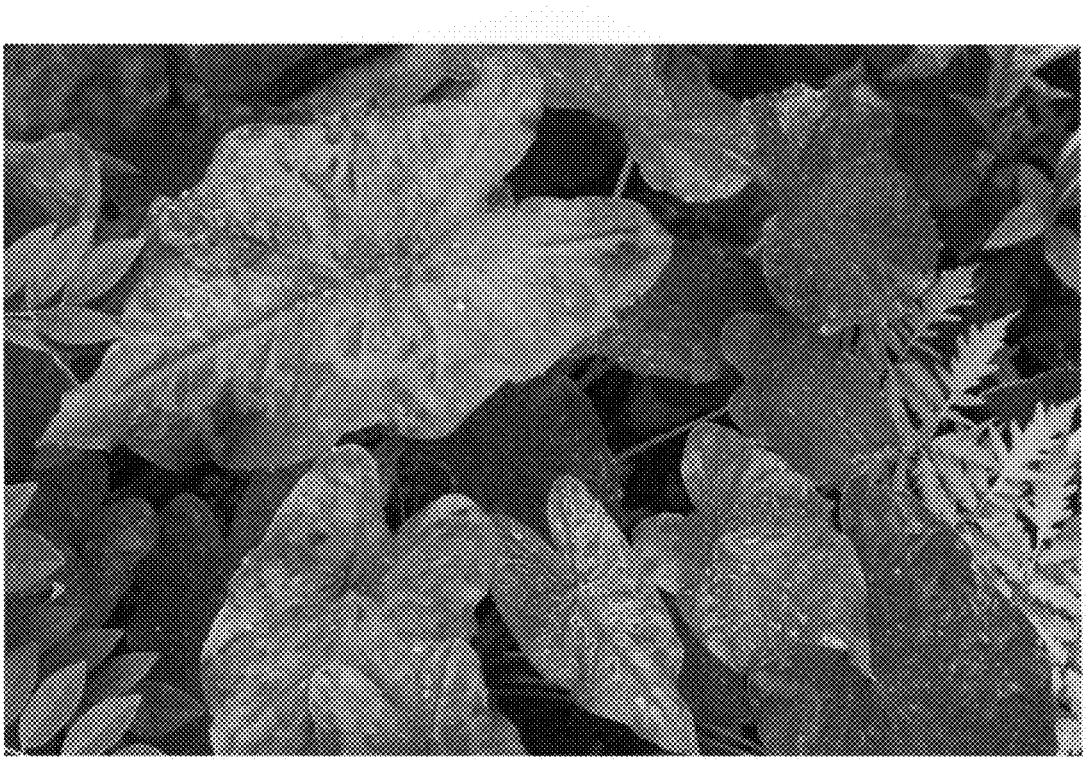

The photograph in FIG. 2 provides a close-up view of the younger foliage of 'Poison Dart Frog'.

The colors in the photographs are as close as possible with the digital photography techniques available, the color values cited in the detailed botanical description accurately describe the colors of the new *Caladium*.

DETAILED BOTANICAL DESCRIPTION OF THE PLANT

The following is a detailed description of three year-old plants of the new cultivar plants as grown outdoors, in full sun, under 2 mm poly in Louisville, Ky. The phenotype of the new cultivar may vary with variations in environmental, climatic, and cultural conditions, as it has not been tested under all possible environmental conditions. The color determination is in accordance with The 2007 R.H.S. Colour Chart of the Royal Horticultural Society, London, England, except where general color terms of ordinary dictionary significance are used.

General description:

*Plant type*.—Herbaceous tropical perennial.

*Plant habit*.—Upright, stemless, compact.

*Height and spread*.—Reaches 30 to 60 cm in both height and width.

*Cold hardiness*.—At least to U.S.D.A. Zone 9.

*Diseases and pests*.—No particular resistance and susceptibility to diseases or pests has been observed.

*Roots*.—Fleshy.

*Propagation type*.—In vitro propagation.

*Growth rate*.—Vigorous.

*Time required for root development*.—An average of 14 days for root initiation with a rooted cutting produced after an average of 35 days.

*Stem description*.—Stemless, can produce large tubers with age.

*Tuber description*.—Fleshy and not freely branched, irregular globose in shape, an average of 6.5 cm in diameter, color; a blend between 183A and 200A.

Foliage description:

*Leaf shape*.—Sagittate.

*Leaf division*.—Single.

*Leaf base*.—Hastate.

*Leaf apex*.—Acute and cuspidate.

*Leaf venation*.—Pinnate, color: upper young and lower surface; matches leaf coloration, mature upper and lower surface 138B.

*Leaf margins*.—Undulate.

*Leaf attachment*.—Petiolate.

*Leaf arrangement*.—Emerge from tuber.

*Leaf surface*.—Upper surface and lower surface; coriaceous and glabrous.

*Leaf orientation*.—Held horizontal to petiole.

*Leaf color*.—Young foliage: upper and lower surface; 144A to 144B with blotches of 58B and small occasional spots of 155B, maturing foliage upper and lower surface; 137B with blotches of 58B and occasional small spots of 155B.

*Leaf size*.—An average of 22 cm in length and 12 cm in width.

*Petioles*.—Held erect to semi-erect, an average of 45 cm in length and 6 mm in distal diameter and 14 mm in proximal diameter, glaucescent surface, color; 144D lightly suffused with 183A, tuber-like trunk; formed at the base of the petioles with age, about 7 cm in length and 11 cm in width on a 2 year-old plant, comprised of petiole scales, surface is rough and paper-like, color is a blend of N199B and N199D, petiole wings are absent.

Inflorescence description:

*Inflorescence type*.—Spadix surrounded by a spathe, male portion held above female portion, only female flowers are developed.

*Inflorescence size*.—An average of 15 cm in length and 3 cm in width.

*Inflorescence bud*.—Linear to slightly narrow oblanceolate in shape, an average of 12 cm in length and 3 cm in width.

*Flower fragrance*.—None.

*Lastingness of inflorescence*.—Inflorescence blooms intermittently during the bloom period, individual flowers last about 2 to 3 weeks.

*Inflorescence/flower quantity*.—An average of 100 female flowers sessile to spadix, sessile male flowers are undeveloped.

*Spathe*.—Hooded, bract, subtending spadix, an average of 15.5 cm in length and 3.5 cm in width, entire margin, bottom portion; elliptic in shape, an average of 9.5 cm in length and 3 cm in width, apex fused to upper portion, upper portion (hood); oval in shape, an average of 6 cm in length and 4 cm in width, acute apex, upper and lower portion inner and outer surface; coriaceous, smooth, and striate, color lower portion outer surface; 144A to 144C and inner surface; 144D with N186B to 186C near the base, color upper portion inner surface; 157D and outer surface; a blend between 150D and 157A, color fades to 199B to 199D.

*Spadix*.—Male portion above female zone, upright linear to slightly narrow oblanceolate in shape (phallus like), apex narrowly pointed, an average of 12 cm in length, male portion; an average of 8.5 cm in length and 9 mm in width, female portion; an average of 2 cm in length and 1 cm in width, color; male portion 176A and female portion 165B to 165D.

*Peduncle*.—Grows from base of plant, triangular in shape, an average of 20 cm in length and 8 mm in diameter, durable and strong, a blend of 144C, 184A, and 197A, glabrous and smooth surface.

Reproductive organs:

*Gynoecium*.—2 pistils, 4 stigmas are N92A in color, bicarpellate ovary is full of many minute ovules cylindric in shape and 155D in color.

*Androcoecium*.—Undeveloped.

*Fruit and seed*.—Sterile.

It is claimed:

1. A new and distinct cultivar of *Caladium* plant named 'Poison Dart Frog' as herein illustrated and described.

* * * * *